(12) United States Patent
Yang et al.

(10) Patent No.: US 11,245,111 B2
(45) Date of Patent: Feb. 8, 2022

(54) STABLE POSITIVE SIDE MATERIAL FOR ALL-ORGANIC FLOW BATTERY

(71) Applicant: UNIVERSITY OF SOUTHERN CALIFORNIA, Los Angeles, CA (US)

(72) Inventors: Bo Yang, Los Angeles, CA (US); G. K. Surya Prakash, Hacienda Heights, CA (US); Robert Aniszfeld, Los Angeles, CA (US); Sri R. Narayan, Arcadia, CA (US); Lena Hoober-Burkhardt, Los Angeles, CA (US); Sankarganesh Krishnamoorthy, Los Angeles, CA (US); Advaith Murali, Los Angeles, CA (US); Archith Nirmalchandar, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 124 days.

(21) Appl. No.: 16/161,647

(22) Filed: Oct. 16, 2018

(65) Prior Publication Data
US 2019/0115594 A1    Apr. 18, 2019

Related U.S. Application Data

(60) Provisional application No. 62/573,292, filed on Oct. 17, 2017.

(51) Int. Cl.
*H01M 4/36* (2006.01)
*H01M 8/18* (2006.01)
*H01M 4/60* (2006.01)
*H01M 8/08* (2016.01)
*C07C 309/44* (2006.01)
*C07C 309/42* (2006.01)
*C07C 309/43* (2006.01)
(Continued)

(52) U.S. Cl.
CPC .......... *H01M 4/368* (2013.01); *C07C 303/08* (2013.01); *H01M 4/60* (2013.01); *H01M 8/08* (2013.01); *H01M 8/188* (2013.01); *C07C 309/42* (2013.01); *C07C 309/43* (2013.01); *C07C 309/44* (2013.01); *C07C 2603/24* (2017.05); *C07C 2603/50* (2017.05); *H01M 2004/028* (2013.01); *H01M 2008/1095* (2013.01); *H01M 2300/0002* (2013.01); *H01M 2300/0082* (2013.01)

(58) Field of Classification Search
CPC .......... H01M 4/60; H01M 4/36; H01M 4/368; H01M 8/18; H01M 8/188; H01M 8/08; C07C 309/42; C07C 309/43; C07C 309/44
See application file for complete search history.

(56) References Cited

U.S. PATENT DOCUMENTS 9,614,245 B2 * 4/2017 Narayan ................. H01M 8/20
2015/0243991 A1 * 8/2015 Huskinson .............. H01M 4/60
429/72

* cited by examiner

Primary Examiner — Karie O'Neill Apicella
(74) Attorney, Agent, or Firm — Brooks Kushman P.C.

(57) ABSTRACT

A quinone derivative with a high redox potential that does not undergo Michael addition or proto-desulfonation. This molecule addresses the key issues faced with the positive side material of an aqueous all-organic flow battery. This new molecule is 2,5-dihydroxy-4,6-dimethylbenzene-1,3-disulfonic acid (or the disulfonate salt thereof). This quinone derivative offers good solubility, electrochemical reversibility, and robustness to charge/discharge cycling. Quinones with reduced crossover are also provided.

15 Claims, 9 Drawing Sheets

(51) Int. Cl.
 *C07C 303/08* (2006.01)
 *H01M 8/1018* (2016.01)
 *H01M 4/02* (2006.01)

STABLE POSITIVE SIDE MATERIAL FOR ALL-ORGANIC FLOW BATTERY

CROSS-REFERENCE TO RELATED APPLICATIONS

This application claims the benefit of U.S. provisional application Ser. No. 62/573,292 filed Oct. 17, 2017, the disclosure of which is hereby incorporated in its entirety by reference herein.

STATEMENT REGARDING FEDERALLY SPONSORED RESEARCH OR DEVELOPMENT

This invention was made with government support under DE-AR0000353 awarded by the Department of Energy/ARPA. The government has certain rights in the invention.

TECHNICAL FIELD

The present invention is related to metal-free organic redox flow batteries.

BACKGROUND

Organic redox flow batteries are particularly attractive for meeting the demanding performance, cost and sustainability requirements for grid-scale energy storage. It is widely known that the intermittency of renewable energy generation from solar and wind resources necessitates that large-scale energy storage be available for load-shifting or peak-shaving on the grid, at sub-station, and even at residences. With an estimated global electricity production of about 50-60 Terawatt hours/day, even if only 20% of this energy is stored, deployment of 10-15 Gigatons of batteries over a 15-year period assuming a modest specific energy of 50 Wh/kg is required. A point of reference for the scale of assessing this demand is that it is five times as large as the world's iron and steel industry in that 2.8 Gigatons of iron ore is mined every year worldwide. The astonishing magnitude of this demand for batteries for grid-scale energy storage imposes the most stringent requirements not only on cost and durability, but also on eco-friendliness and sustainability. The requirement of eco-friendliness and sustainability has only been recently emphasized in the Department of Energy's approach to new technology solutions.

The capital cost of a battery system is largely determined by the materials cost, complexity of the system design, and performance features such as—energy density, power density, durability, and efficiency. Sustainability is determined by resource limitations, eco-friendliness of the manufacturing and recycling processes. Although some of the more mature systems like vanadium redox and zinc-chlorine are gradually moving towards large-scale implementation, the high associated expenses mandate cost reductions. Moreover, some of the prior art battery technologies use heavy metals such as vanadium and/or chromium which are environmentally undesirable. Iron-air and manganese dioxide-carbon systems are promising from a cost and sustainability standpoint. However, these technologies are not based on renewable resources thereby rendering their long-term sustainability uncertain. It should be appreciated that a battery based on carbon resources that avoids the use of metals can provide long-term sustainability in addition to being inexpensive.

Various quinone-type molecules that are suitable for use in an all-organic flow battery area have been investigated. However, some of these molecules were prone to degradation reactions by way of the Michael reaction with water or by proto-desulfonation.

Accordingly, there is a need for improved redox flow battery systems that are eco-friendly while using inexpensive material.

SUMMARY

In at least one embodiment, the present invention solves one or more problems of the prior art by providing a quinone derivative with a high redox potential that does not undergo Michael addition or proto-desulfonation. This molecule addresses the key issues faced with the positive side material of an aqueous all-organic flow battery. This new molecule is 2,5-dihydroxy-4,6-dimethylbenzene-1,3-disulfonic acid (or the disulfonate salt thereof). This quinone derivative offers good solubility, electrochemical reversibility, and robustness to charge/discharge cycling.

DETAILED DESCRIPTION

Figure 1:
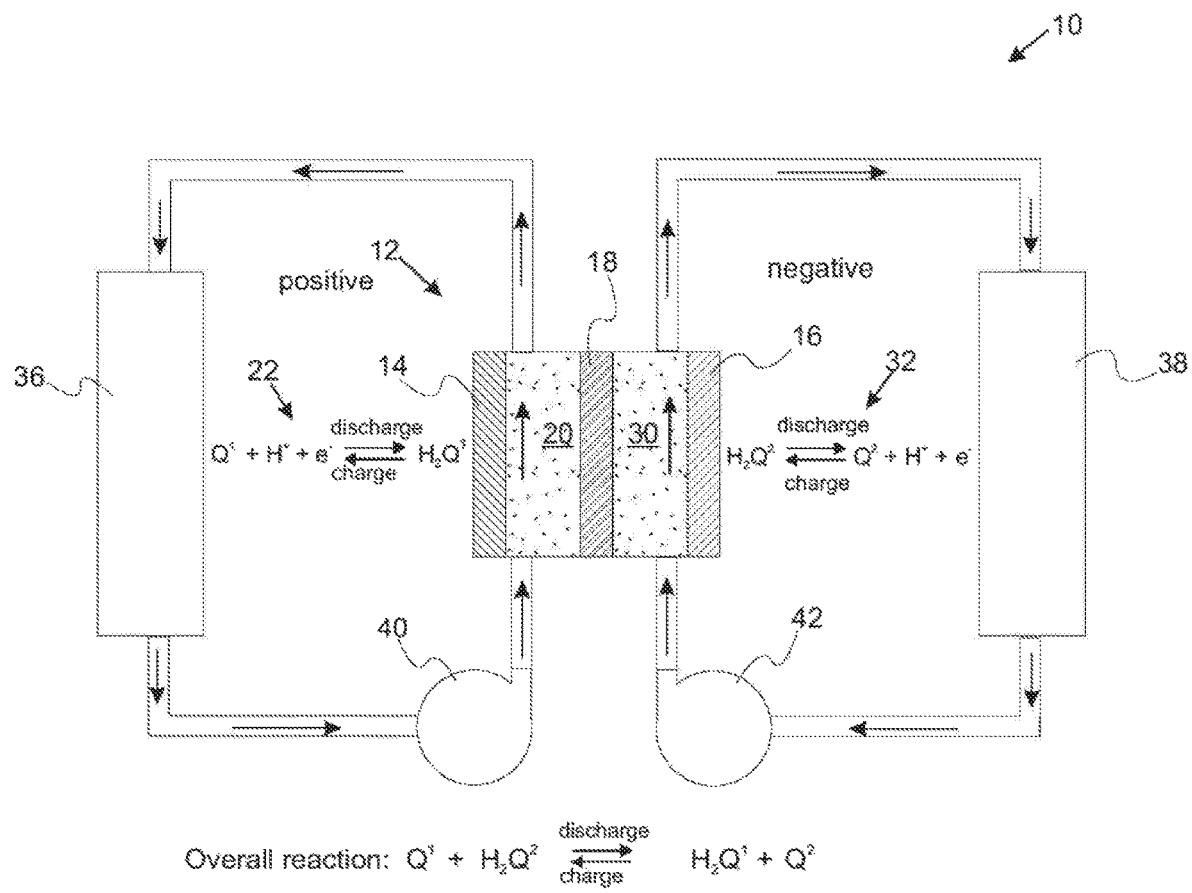
FIG. 1. A schematic illustration of a flow battery that includes electrolytes that include quinones and hydroquinones.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include alkyl, lower alkyl, $C_{1-6}$ alkyl, $C_{6-10}$ aryl, or $C_{6-10}$ heteroaryl; single letters (e.g., "n" or "o") are 1, 2, 3, 4, or 5; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

As used herein "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. The alkyl group can be optionally substituted (i.e., a "substituted alkyl") with another atom or functional group such as alkyl, substituted alkyl, halogen, aryl, substituted aryl, alkoxyl, hydroxyl, nitro, amino, alkylamino, dialkylamino, sulfate, mercapto, and the like.

As used herein "aryl" means a monovalent aromatic hydrocarbon having a single ring (i.e., phenyl) or fused rings (i.e., naphthalene). In a refinement, such aryl groups include from 6 to 12 carbon ring atoms. In another refinement, such aryl groups include 6 to 10 carbon ring atoms. Representative aryl groups include, by way of example, phenyl biphenyl, naphthyl, anthranyl, and naphthalene-1-yl, naphthalene-2-yl, and the like. The term "arylene" means a divalent aryl group.

As used herein "heteroaryl" means a monovalent aromatic group having a single ring or two fused rings and containing in the ring at least one heteroatom (typically 1 to 3 heteroatoms) selected from nitrogen, oxygen or sulfur. In a refinement, heteroaryl groups typically contain from 5 to 10 total ring atoms. In a refinement, heteroaryl groups have from 6 to 16 total ring atoms. In a refinement, the heteroaryl is a $C_{5-12}$ heteroaryl. Examples of heteroaryl include, but are not limited to, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. Additional examples heteroaryl groups include, but are not limited to, furanyl, thienyl, and pridinyl group. The term "heteroarylene" means a divalent heteroaryl group.

It should be appreciated that each C—H bond in the formulae set forth herein can be substituted. For example, each C—H bond can be substituted by halo, cyano, nitro, hydroxyl, $C_{1-10}$ alkyl, $C_{1-8}$ alkoxyl, $C_{6-14}$ aryl, $C_{5-13}$ heteroaryl, $NH_2SO_2R$, $CF_3$, o-$OCH_3$, pyridinyl, phenyl, —CHO, —COR—, $NH_2$, —NHR, —N(R)$_2$, —O$^-$M$^+$, —NHCOR, —OR, —CH$_3$, —C$_2$H$_5$, —NO$_2$, —N(R)$_3^+$X$^-$, —CF$_3$, CCl$_3$, —CN, —SO$_3$H, —PO$_3$H$_2$, —COOH, —OH, —O$^-$M$^+$, —SO$_3^-$M$^+$, —PO$_3^{2-}$M$^+_2$, —COO$^-$M$^+$, —COOR, F, Cl, Br, —CHO, or —COR where R is H or $C_{1-10}$ alkyl and M$^+$ is a positively charged counter-ion (e.g., Na$^+$, K$^+$, and the like). Such substituted C—H bonds can be symbolized by C—R$_z$ where z is an integer from 1 to 100 that has not already been used as a subscript or subscript for an R group.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100.

Abbreviations

"AQDS" means anthraquinone-2,7-disulfonic acid.

"DMDHMS" means 2,6-dimethyl-1,4-dihydroxybenzene-3-sulfonic acid.

"RDE" means rotating disk electrode.

With reference to FIG. 1, a schematic illustration of a flow battery that includes a pair of organic redox couples is provided. Flow battery 10 includes battery cell 12 which includes positive electrode 14, negative electrode 16, and polymer electrolyte membrane 18. In the context of a flow cell, reduction occurs during discharge at the positive electrode and oxidation occurs during discharge at the negative electrode. Conversely, oxidation occurs during charging at the positive electrode and reduction occurs during charging at the negative electrode. Polymer electrolyte membrane 18 is interposed between positive electrode 14 and negative electrode 16. Positive electrode electrolyte 20 includes water and a first redox couple 22. In FIG. 1, a first quinone redox couple is depicted as an example. Positive electrode electrolyte 20 flows over and contacts positive electrode 14. First redox couple 22 includes a first organic compound $Q^1$ and a reduction product $H_2Q^1$ of the first organic compound. The first organic compound $Q^1$ is a fully substituted sulfonated quinone. During discharge of the flow battery, the first organic compound $Q^1$ is reduced to the first reduction product $H_2Q^1$ of the first organic compound. During charging of the flow battery, the first reduction product $H_2Q^1$ is oxidized to the first organic compound $Q^1$. Negative electrode electrolyte 30 includes water and a second redox couple 32. Negative electrode electrolyte 30 flows over and contacts the negative electrode 16. In FIG. 1, a second quinone redox couple is depicted as an example.

The second redox couple 32 includes a second organic compound $Q^2$ and a reduction product $H_2Q^2$ of the second organic compound. During discharge, the reduction product $H_2Q^2$ is oxidized to the second organic compound $Q^2$. In a refinement, the first organic compound (e.g., first quinone) has a standard electrode potential that is at least 0.3 volts higher than a standard electrode potential (e.g., MSE) for the second organic compound (e.g., the second quinone). Compounds having standard electrode potential greater than 0.3 relative to a standard electrode potential (e.g., MSE or standard hydrogen electrode) are useful in the negative electrode electrolyte while compounds having standard electron potentials less than 0.3 relative to a standard electrode potential (e.g., MSE or standard hydrogen electrode) are useful in the positive electrode electrolyte.

Still referring to FIG. 1, flow battery 10 further includes a positive electrode reservoir 36 in fluid communication with the positive electrode 14. The positive electrode electrolyte 20 is stored in the positive electrode reservoir 36 to charge and discharge the flow battery. The positive electrode electrolyte cycles through battery cell 12 from positive electrode reservoir 36 via the pumping action of pump 40. A negative electrode reservoir 36 is in fluid communication with the negative electrode 16. The negative electrode electrolyte 30 is stored in the negative electrode reservoir 36 to charge and discharge the flow battery. The negative electrode electrolyte cycles through battery cell 12 from negative electrode reservoir 38 via the pumping action of pump 42.

In one variation, the first organic compound $Q^1$ is selected from the group consisting of compounds having formulae 1, and 2 and the reduction product $H_2Q^1$ is selected from the group of compounds having formulae 1', and 2':

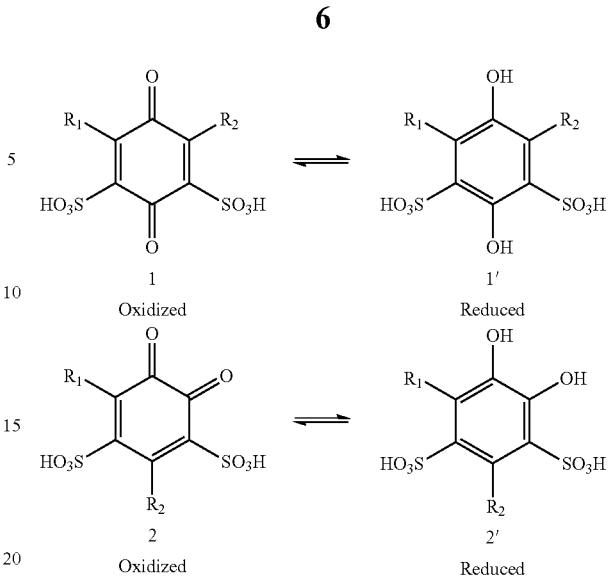

wherein $R_1$, $R_2$ can be electron withdrawing groups or electron donating groups depending on the desired electrode potential. Examples of such electron withdrawing groups include but are not limited to, $-NO_2$, $-N(R_3)_3{}^+X^-$, $-CF_3$, $CCl_3$, $-CN$, $-SO_3H$, $-PO_3H_2$, $-COOH$, $-OH$, $-O^-M^+$, $-SO_3{}^-M^+$, $-PO_3{}^{2-}M^+{}_2$, $-COO^-M^+$, $-COOR_3$, F, Cl, Br, $-CHO$, or $-COR_3$ where $R_3$ is H or $C_{1-10}$ alkyl, $M^+$ is a positively charged counter-ion (e.g., $Na^+$, $K^+$, and the like). Examples of such electron donating groups include but are not limited to, $C_{1-10}$ alkyl, $NH_2$, $-NHR_2$, $-N(R_2)_2$, $-O^-M^+$, $-NHCOR_2$, $-OR_2$, $-CH_3$, $-C_2H_5$, or phenyl where $R_2$ is H or $C_{1-10}$ alkyl and $M^+$ is a positively charged counter-ion (e.g., $Na^+$, $K^+$, or the like). In a refinement, $R_1$, $R_2$ are each independently H, aryl, heteroaryl, $C_{1-10}$ alkyl, $NH_2$, $-NHR_3$, $-N(R_3)_2$, $-O^-M^+$, $-NHCOR_3$, $-OR_3$, $-CH_3$, $-C_2H_5$, $-SO_3H$, $-PO_3H_2$, $-COOH$, $-OH$, $-N(R_2)_3{}^+X^-$, $-CF_3$, $CCl_3$, $-CN$, $-COOR_3$, F, Cl, Br, $-CHO$, $-COR_2$, $-O^-M^+$, $-SO_3{}^-M^+$, $-PO_3{}^{2-}M^+{}_2$, $-COO^-M^+$, pyridinyl, imidazoyl, pyrroyl, or phenyl where $R_3$ is H or $C_{1-10}$ alkyl and $M^+$ is a positively charged counter-ion (e.g., $Na^+$, $K^+$, and the like).

In another variation, the first organic compound $Q^1$ is a "bulky" quinone that resists crossover. In this variation, the first organic compound $Q^1$ is selected from the group consisting of compounds having formulae 1, and 2 and the reduction product $H_2Q^1$ is selected from the group of compounds having formulae 1', and 2':

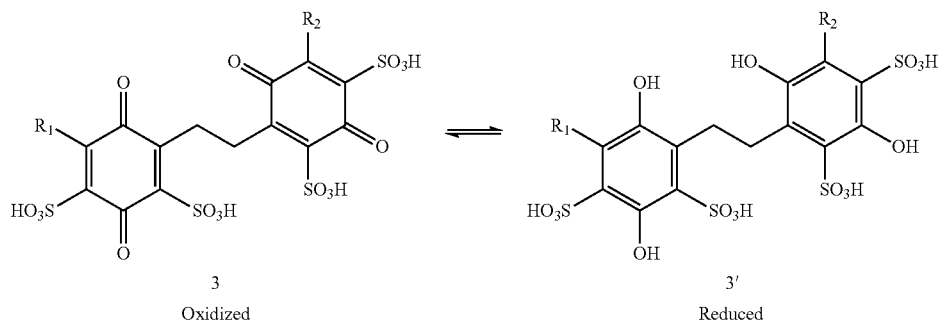

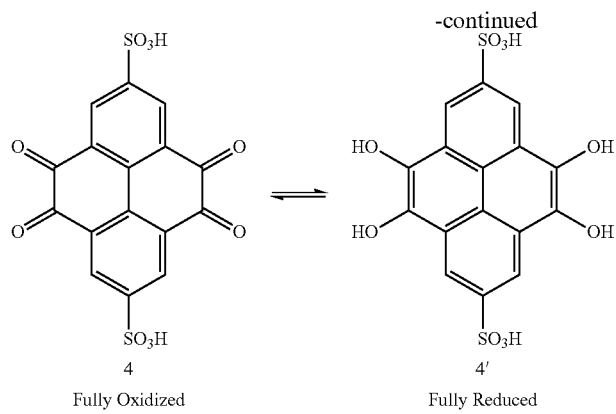

4 Fully Oxidized ⇌ 4' Fully Reduced wherein $R_1$, $R_2$ are as set forth above.

In a refinement, the negative electrode electrolyte 20 of flow battery 10 includes second organic compound $Q^2$ and a reduction product $H_2Q^2$ of the second organic compound. Virtually, any suitable couple can be used for second organic compound $Q^2$. Suitable examples of which are found in U.S. Pat. No. 9,614,245; the entire disclosure of which is hereby incorporated by reference. In a refinement, the second couple includes a sulfonated anthraquinone. Particularly, useful examples for $Q^2$ include anthraquinones having formulae 5, 6, and 7 with $H_2Q^2$ being the reduced compounds thereof.

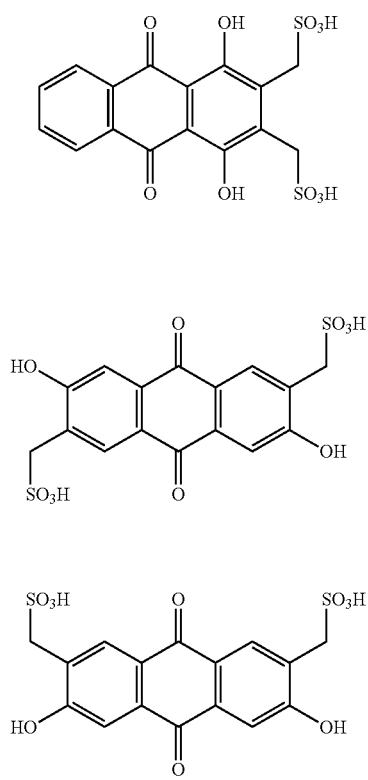

The following examples illustrate the various embodiments of the present invention. Those skilled in the art will recognize many variations that are within the spirit of the present invention and scope of the claims.

Method of Preparation of 2,5-dihydroxy-4,6-dimethylbenzene-1,3-disulfonic acid (or the Disulfonate Salt), Abbreviated as DHDMDS The following chemical reaction scheme represents the various steps in the preparation of the DHDMDS.

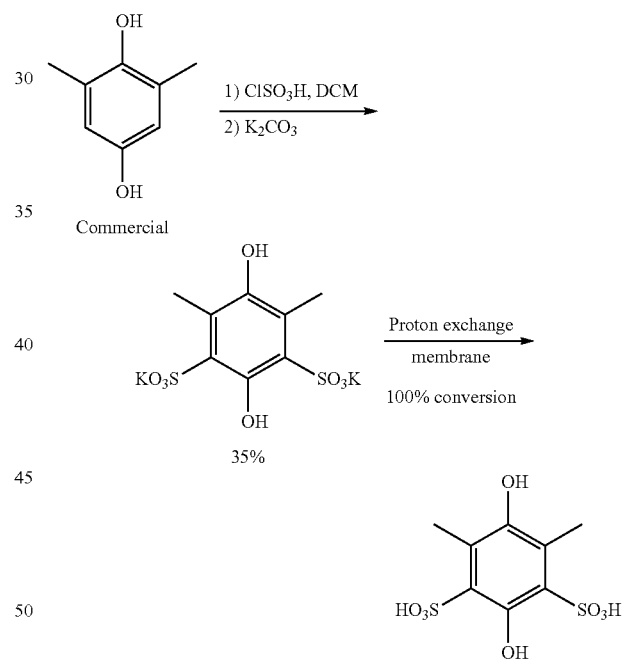

Figure 2:
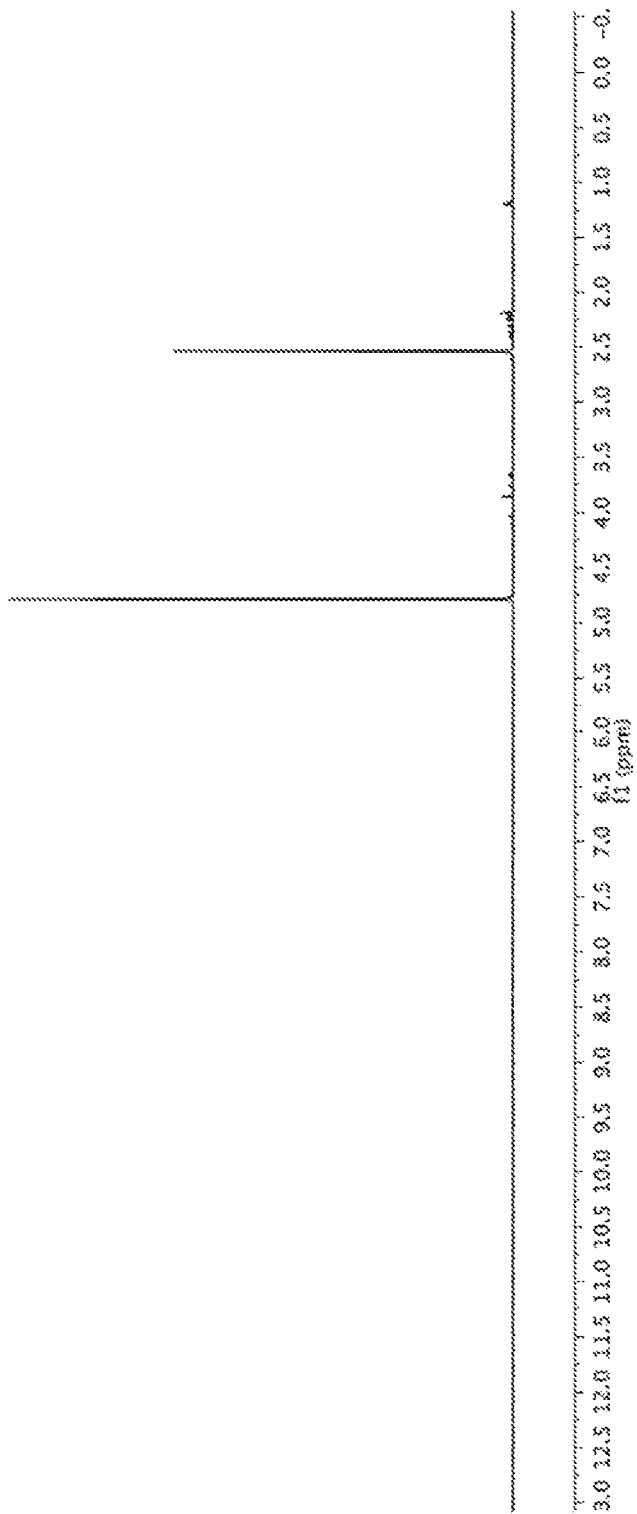
FIG. 2. Spectra 1 1H NMR (D2O) in the potassium form.
Figure 3:
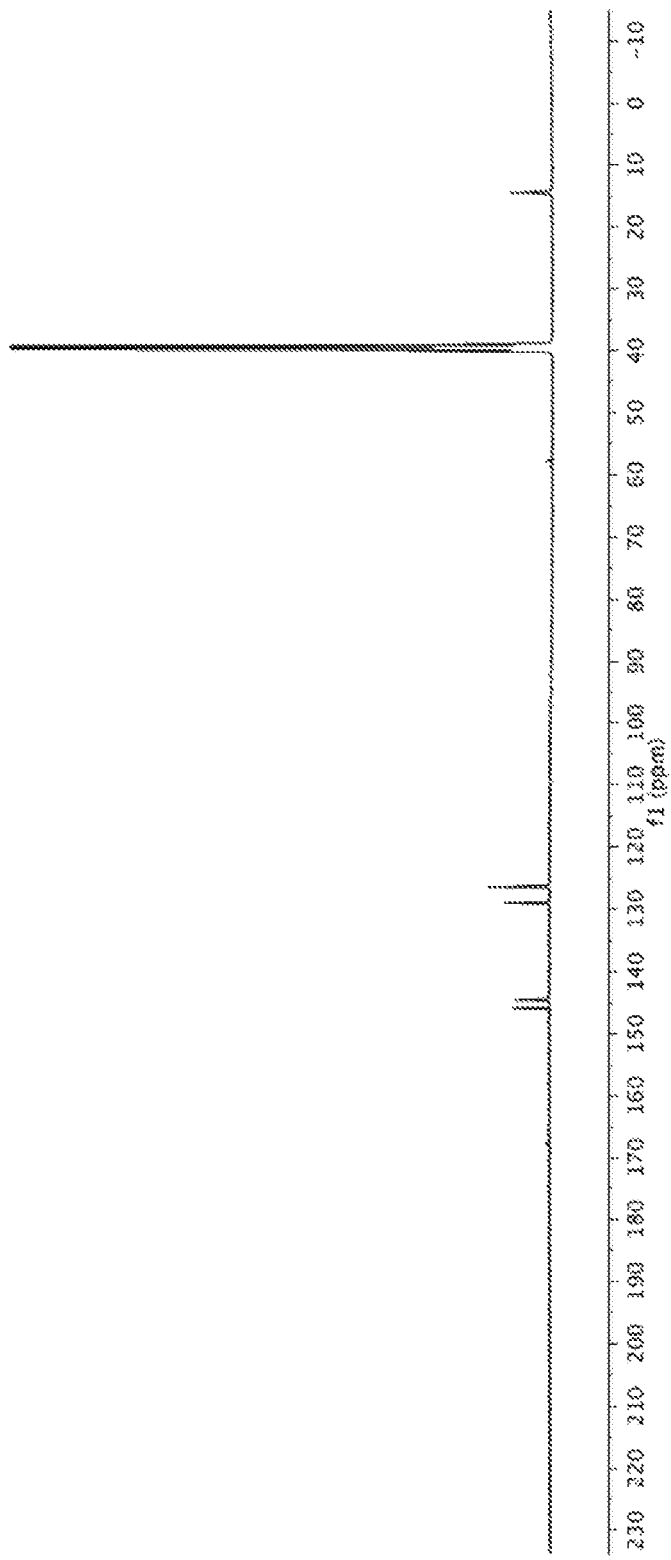
FIG. 3. Spectra 2 13C NMR (DMSO-d6) of DHDMDS in the potassium form.

Dichloromethane (anhydrous 200 mL) and $ClSO_3H$ (40 mL, 6 equiv, 600 mmol) were mixed in 500 mL Schlenk flask containing magnetic stir bar in $N_2$ glove bag. The flask was connected to nitrogen line and the 2,6-dimethyl-1,4-dihydroxybenzene (100 mmol, 13.8 g) against the stream of Nitrogen (evolution of HCl). Once the effervescence stopped, the flask was closed and stirred vigorously under nitrogen atmosphere. The reaction was monitored by $^1H$ NMR. After 26 hours, the reaction was allowed to stand, and separation of DCM layer and a greenish thick oily layer was observed. The DCM layer was carefully decanted under $N_2$ atm. Greenish oily residue was stirred with anhydrous DCM (2×100 mL) and decanted. The greenish oily liquid was poured on ice and washed with ice-water. This mixture was quenched with solid $K_2CO_3$ to get a neutral pH. This mixture was treated with acetone (30-40%) and cooled in ice to get a white precipitate, which was filtered and washed with 30% acetone/water. To the resulting solution, 200 mL acetone was added and no precipitation was observed. This solution was rotary evaporated to minimize the solvent and allowed to stand in the fridge. No crystallization was observed. The solution was completely dried by rotary evaporation to get beige solid, which was azeotroped with EtOH and dried under high vacuum. $^1$H NMR of the mixture showed signal around 2.22 ppm, which was only removed by treating the solid with EtOH (3×150 mL) to get >97% by $^1$H NMR. When the solid was calibrated with imidazole internal standard, it appeared to be 65% of the desired product. Therefore, the solid was subjected to extraction with MeOH on a Soxhlet extractor and the solid in regularly analyzed for the presence of the product. After extracting over 48 hours, only traces of the product were found in the solid residue. The MeOH mixture was evaporated to obtain a beige solid (13 g), which was dried under vacuum. Characterized by $^1$H NMR [(500 MHz, Deuterium Oxide) $\delta$ 2.54 (s, 1H)], $^{13}$C NMR [(126 MHz, DMSO-$d_6$) $\delta$ 145.84, 144.50, 129.01, 126.40, 14.38 (q, J=15.7 Hz)] and IR [($cm^{-1}$): 3148.7, 1688.8, 1409, 1183, 1154, 1038, 1006, 742, 656, 595]. (See FIGS. 2 and 3). This solid was dissolved in water and converted to 2,5-dihydroxy-4,6-dimethylbenzene-1,3-disulfonic (DHDMDS) acid using proton exchange column and characterized by cyclic voltammetry and RDE.

Figure 4:
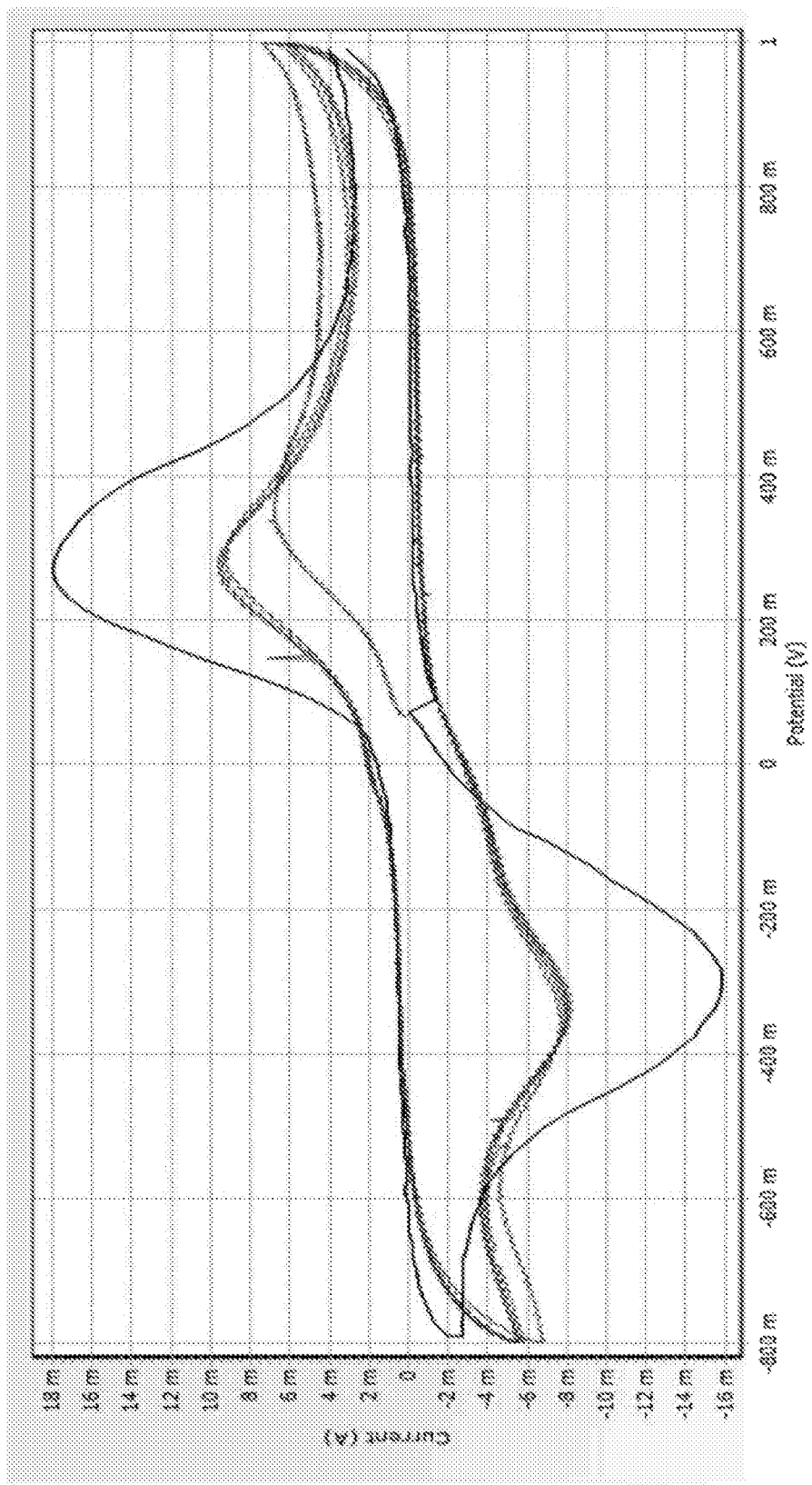
FIG. 4. Cyclic voltammetry of DHDMDS 1) blue—new batch using new method and 2) purple—first batch using old method.

Cyclic Voltammetry studies on the graphite fiber/graphite felt showed that the DHDMDS was electrochemically reversible, as evidenced by the symmetrical current peaks (FIG. 4). Two batches of material were tested and both these batches showed good reversibility.

Figure 5:
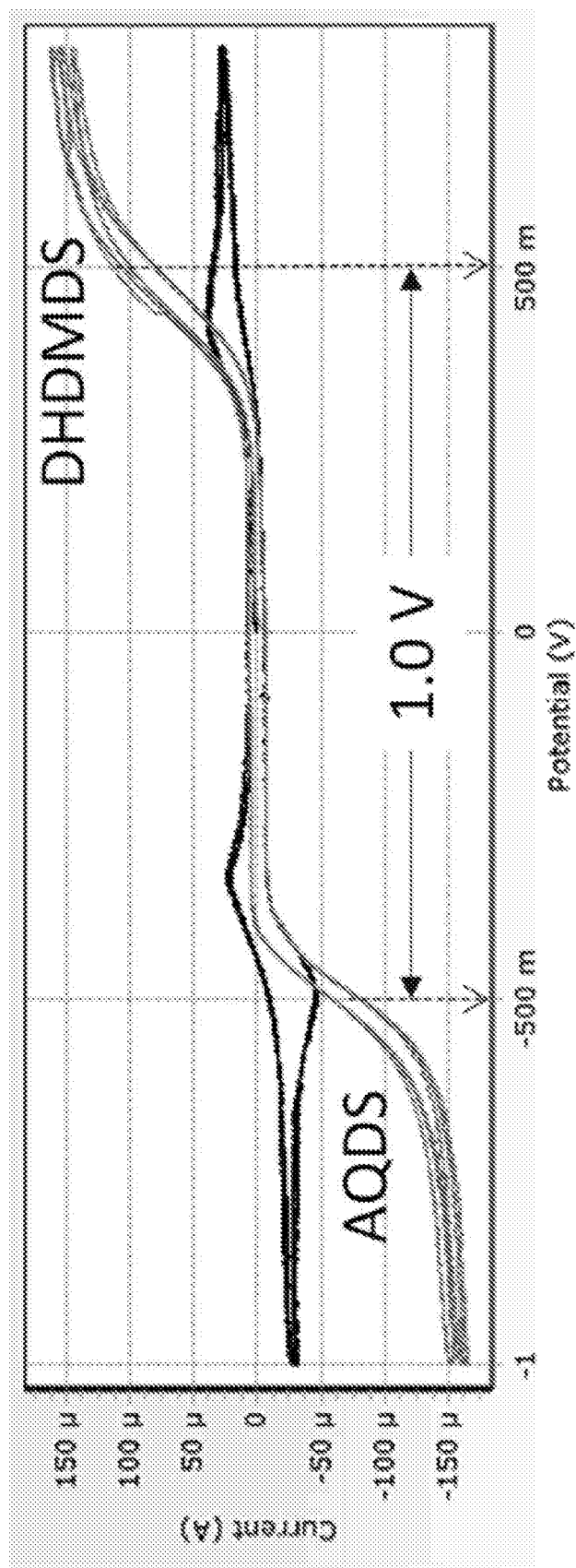
FIG. 5. Cyclic voltammogram and voltammetry at rotating disk electrode for 1 mM DHDMDS and AQDS in 1M sulfuric acid.

The RDE experiments indicate that the material in hand can achieve cell voltage as high as 1V when used against AQDS (FIG. 5).

After the characterization of the DHDMDS, it was utilized in full cell studies employing symmetrical as well as unsymmetrical electrolyte approaches.

Cell Cycling Studies with Symmetrical Electrolyte.

A solution (200 nL) of 0.1M anthraquionedisulfonic acid (AQDS) and 0.1M DHDMDS in 1M $H_2SO_4$ was prepared and split into equal portions and used as electrolytes in the ORBAT. Symmetrical electrolyte refers to the use of the same mixture of electrolyte used on the positive and negative side.

Figure 6:
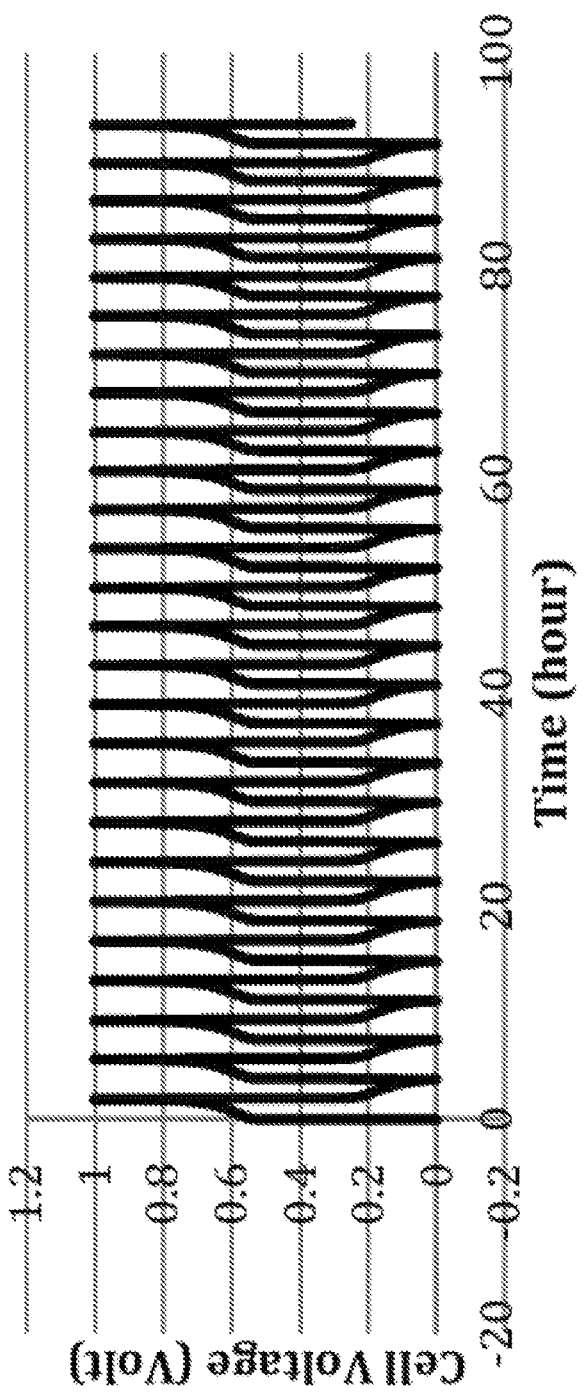
FIG. 6. Cycling at 8 mA/cm2, cell resistance 24 mOhm
Figure 7:
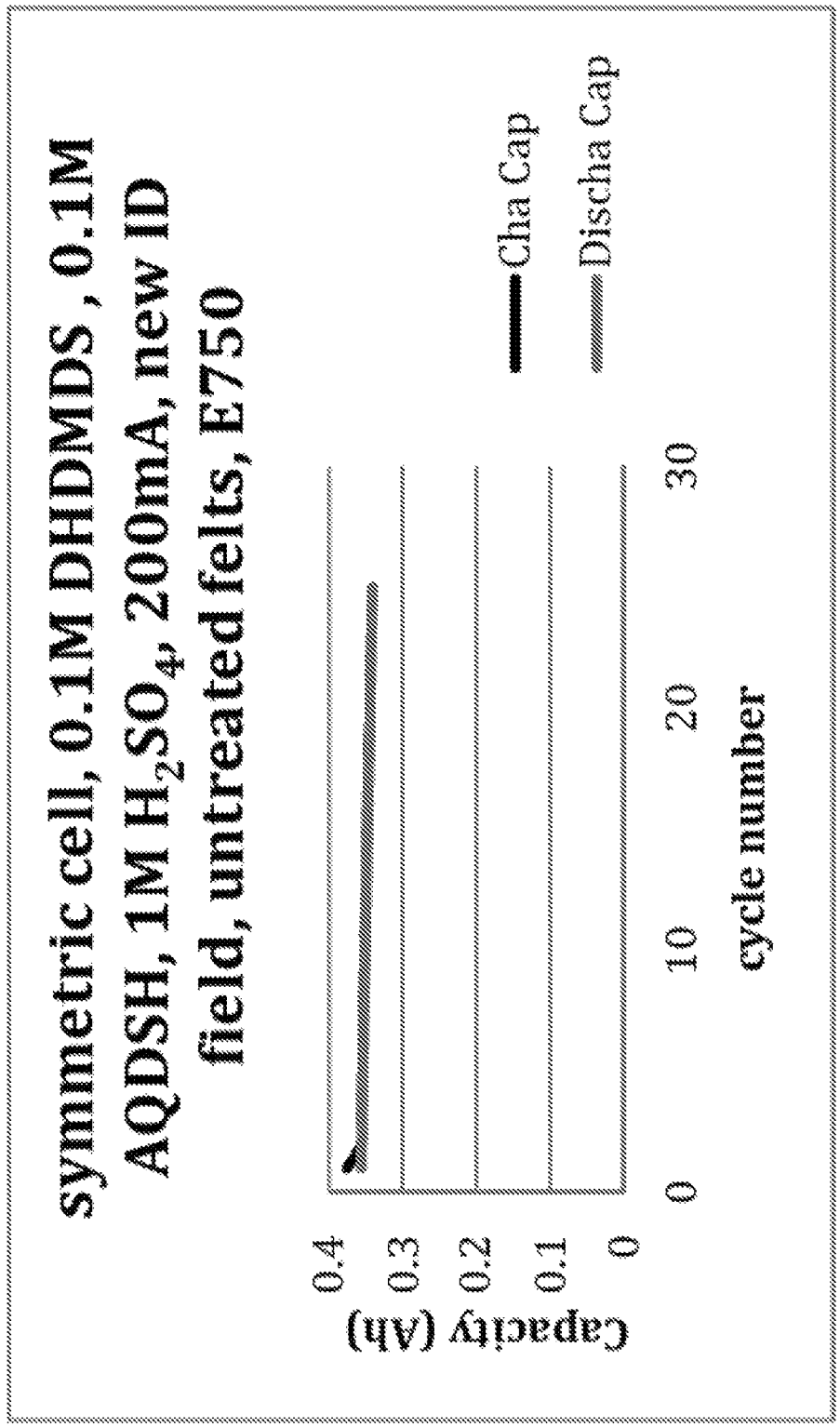
FIG. 7. Capacity Vs Cycles

The charge/discharge cycling of this cell yielded a stable capacity as indicated by the data in FIG. 6. This capacity was maintained constant capacity over 25 cycles (FIG. 7).

Charge/Discharge Cycling in Unsymmetrical Cell.

Figure 8:
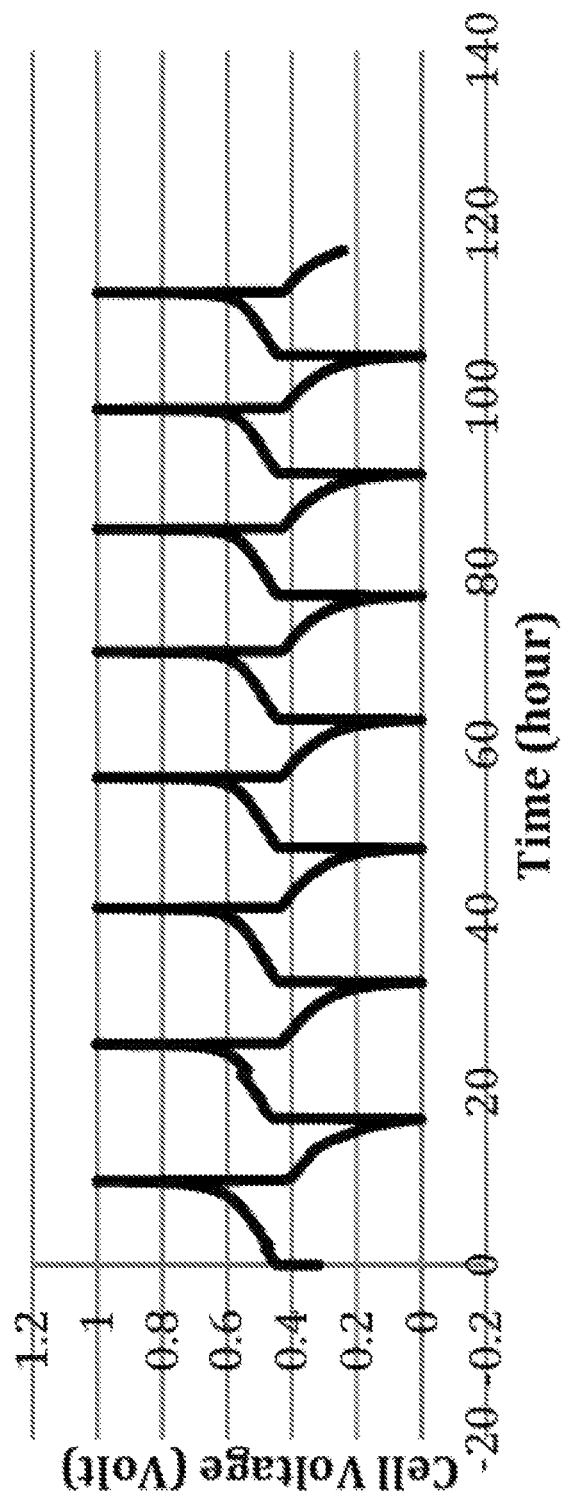
FIG. 8. charge discharge cycles of unsymmetrical cell with AQDS Vs DHDMDS
Figure 9:
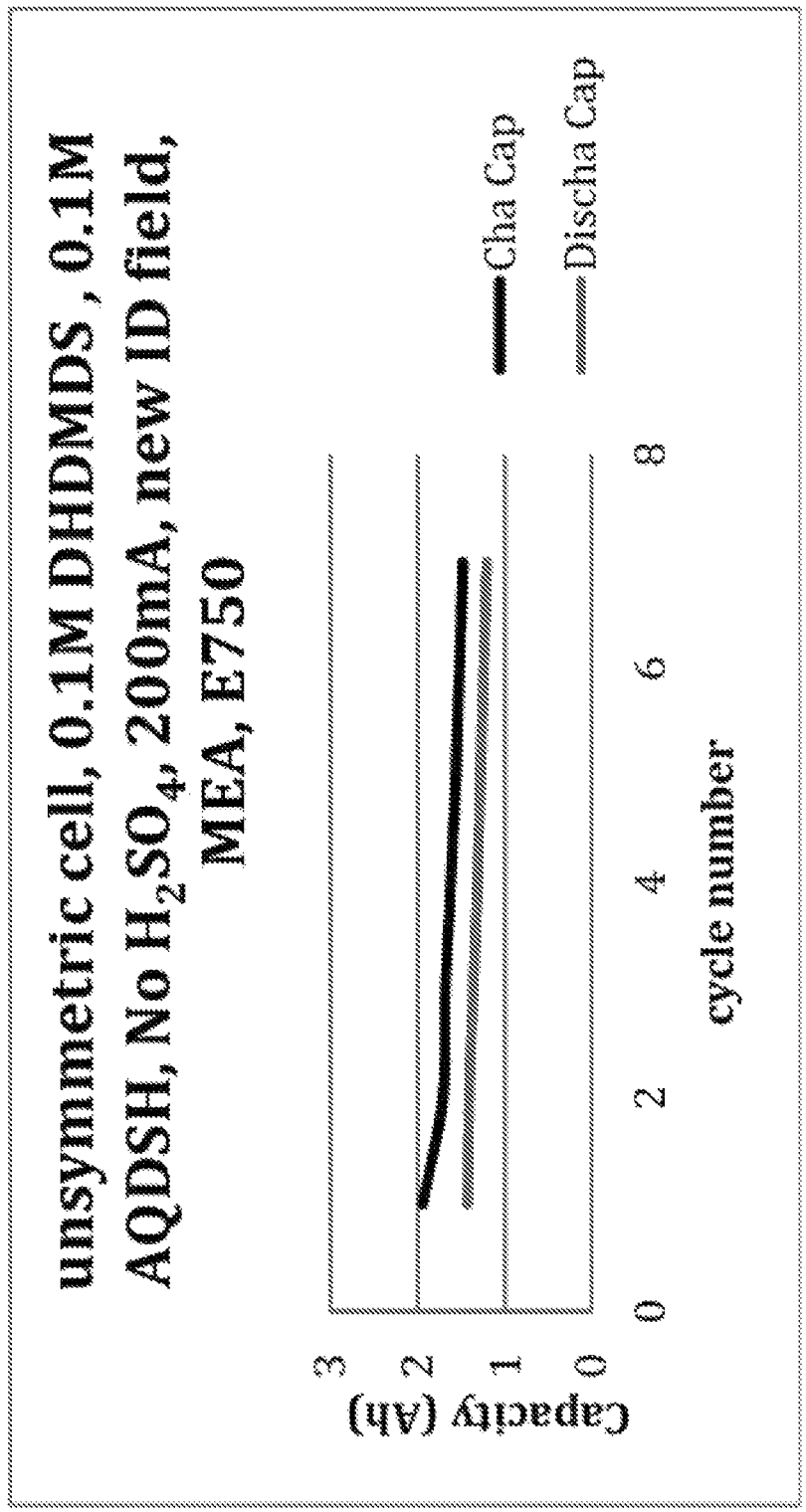
FIG. 9. Capacity Vs cycles of the unsymmetrical AQDS Vs DHDMDS cell

The DHDMDS is also employed to set up an unsymmetrical cell. In this cell, the positive side material was 0.1 M DHDMDS, while the negative side material was 0.1 M AQDS. The cell showed no significant capacity fade confirming that the DHDMDS was a stable positive side material and did not crossover to any significant extent to the negative side. (see, FIGS. 8 and 9).

Proto-Desulfonation Studies.

We determined that the molecule was stable against proto-desulfonation, by heat treatment of 1 M solution of DHDMDS 24 hours in 1M sulfuric acid at 60 degrees Celsius. We found that no decomposition products of the DHDMDS were observed. If decomposition occurred there would be the formation of a precipitate of an insoluble de-sulfonated material. This material is to be contrasted against DHDMBS (2,5-dihydroxy-4,6-dimethylbenzene-1-sulfonic acid) that decomposes readily under similar conditions of heat treatment.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A flow battery comprising:
   a positive electrode;
   a positive electrode electrolyte including water and a first redox couple that includes a first organic compound, the first organic compound being a fully substituted sulfonated quinone, the positive electrode electrolyte flowing over and contacting the positive electrode;
   a negative electrode;
   a negative electrode electrolyte including water and a second redox couple, the negative electrode electrolyte flowing over and contacting the negative electrode; and
   a polymer electrolyte membrane interposed between the positive electrode and the negative electrode, wherein the first organic compound is selected from the group consisting of compounds having formulae 1 and 2 with a reduction product $H_2Q^1$ selected from compounds having formulae 1' and 2', respectively:

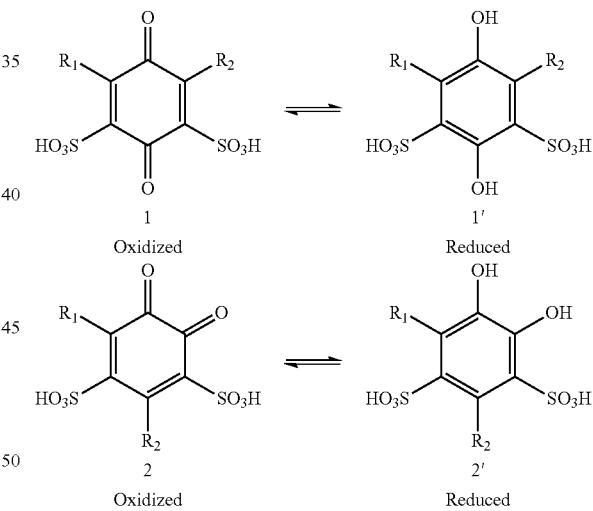

wherein $R_1$, $R_2$ can be electron withdrawing groups or electron donating groups depending on a predetermined electrode potential.

2. The flow battery of claim 1 wherein $R_1$, $R_2$ are each independently selected from the group consisting of —$NO_2$, —$N(R_3)_3^+X^-$, —$CF_3$, —$CCl_3$, —CN, —$SO_3H$, —$PO_3H_2$, —COOH, —OH, —$O^-M^+$, —$SO_3^-M^+$, —$PO_3^{2-}M^+_2$, —$COO^-M^+$, —$COOR_3$, F, Cl, and Br, where $R_3$ is H or $C_{1-10}$ alkyl, $M^+$ is a positively charged counter-ion.

3. The flow battery of claim 1 wherein $R_1$, $R_2$ are each independently selected from the group consisting of $C_{1-10}$ alkyl, $NH_2$, —$NHR_2$, —$N(R_2)_2$, —$NHCOR_2$, —$OR_2$, —$CH_3$, —$C_2H_5$, and phenyl where $R_2$ is H or $C_{1-10}$ alkyl and $M^+$ is a positively charged counter-ion.

4. The flow battery of claim 1 wherein the first organic compound is selected from the group consisting of compounds having formulae 3 and a reduction product $H_2Q^1$ is selected from compounds having formulae 3':

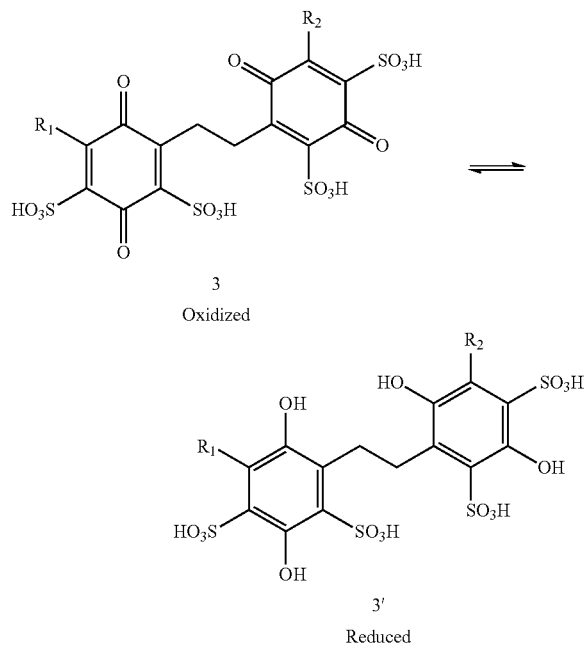

3
Oxidized

3'
Reduced wherein $R_1$ can be an electron withdrawing group or electron donating group depending on a predetermined electrode potential.

5. The flow battery of claim 4 wherein $R_1$ is —$NO_2$, —$N(R_3)_3^+X^-$, —$CF_3$, $CCl_3$, —CN, —$SO_3H$, —$PO_3H_2$, —COOH, —OH, -$O^-M^+$, —$SO_3^-M^+$, —$PO_3^{2-}M^+_2$, —$COO^-M^+$, —$COOR_3$, F, Cl, Br, —CHO, or —$COR_3$ where $R_3$ is H or $C_{1-10}$ alkyl, $M^+$ is a positively charged counter-ion.

6. The flow battery of claim 4 wherein $R_1$ is $C_{1-10}$ alkyl, $NH_2$, —$NHR_2$, —$N(R_2)_2$, —$O^-M^+$, —$NHCOR_2$, —$OR_2$, —$CH_3$, —$C_2H_5$, or phenyl where $R_2$ is H or $C_{1-10}$ alkyl and $M^+$ is a positively charged counter-ion.

7. The flow battery of claim 1 wherein the first organic compound is selected from the group consisting of compounds having formulae 4 and a reduction product $H_2Q^1$ is selected from compounds having formulae 4':

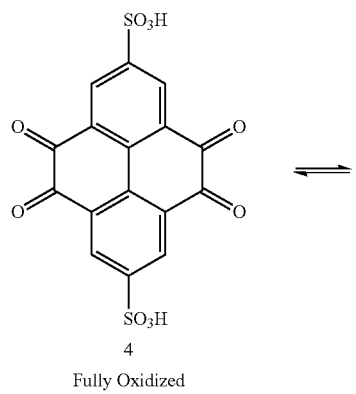

4
Fully Oxidized

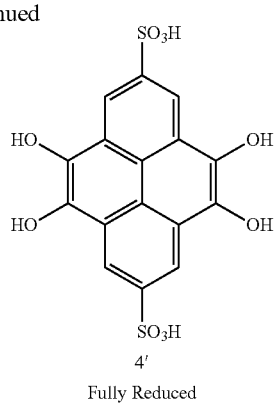

4'
Fully Reduced wherein $R_1$, $R_2$ can be electron withdrawing groups or electron donating groups depending on a predetermined electrode potential.

8. The flow battery of claim 7 wherein $R_1$, $R_2$ are each independently selected from the group consisting of —$NO_2$, —$N(R_3)_3^+X^-$, —$CF_3$, $CCl_3$, —CN, —$SO_3H$, —$PO_3H_2$, —COOH, —OH, —$O^-M^+$, —$SO_3^-M^+$, —$PO_3^{2-}M^+_2$, —$COO^-M^+$, —$COOR_3$, F, Cl, Br, —CHO, —$COR_3$ where $R_3$ is H or $C_{1-10}$ alkyl, $M^+$ is a positively charged counter-ion.

9. The flow battery of claim 4 wherein $R_1$, $R_2$ are each independently selected $C_{1-10}$ alkyl, $NH_2$, —$NHR_2$, —$N(R_2)_2$, —$O^-M^+$, —$NHCOR_2$, —$OR_2$, —$CH_3$, —$C_2H_5$, or phenyl where $R_2$ is H or $C_{1-10}$ alkyl and $M^+$ is a positively charged counter-ion.

10. The flow battery of claim 1 wherein the second redox couple includes a sulfonated anthraquinone.

11. The flow battery of claim 1 wherein the second redox couple includes anthraquinones having formulae 5, 6, and 7 with $H_2Q^2$ being reduced compounds thereof:

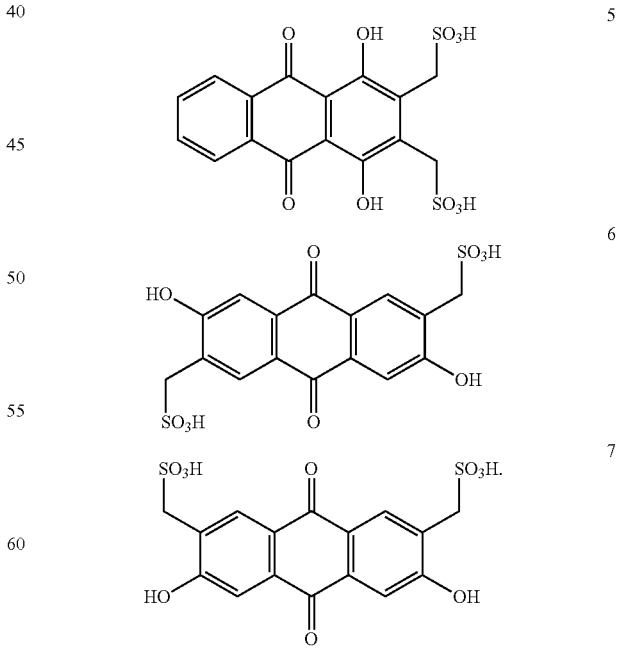

12. The flow battery of claim 1 wherein $R_1$, $R_2$ are each $C_{1-10}$ alkyl.

13. The flow battery of claim 1 wherein $R_1$, $R_2$ are each methyl, ethyl, propyl, or isopropyl.
14. The flow battery of claim 1 wherein first organic compound has the following formula:
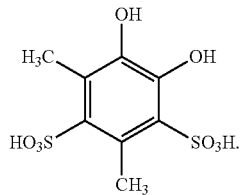
15. The flow battery of claim 1 wherein first organic compound has the following formula:
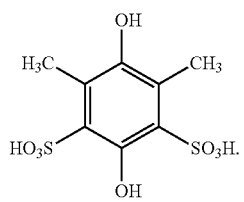
* * * * *

UNITED STATES PATENT AND TRADEMARK OFFICE
CERTIFICATE OF CORRECTION

PATENT NO. : 11,245,111 B2
APPLICATION NO. : 16/161647
DATED : February 8, 2022
INVENTOR(S) : Bo Yang et al.

It is certified that error appears in the above-identified patent and that said Letters Patent is hereby corrected as shown below:

In the Claims

Column 10, Lines 64-65, Claim 3:
After "selected from the group consisting of $C_{1-10}$ alkyl, $NH_2$, $-NHR_2$, $-N(R_2)_2$,"
Insert -- $-O^-M^+$, --.

Signed and Sealed this
Twenty-fourth Day of May, 2022

Katherine Kelly Vidal
*Director of the United States Patent and Trademark Office*